(12) United States Patent
Goetsch et al.

(10) Patent No.: US 7,645,807 B1
(45) Date of Patent: *Jan. 12, 2010

(54) PRODUCTION OF BIODIESEL AND A SIDE STREAM OF CRUDE GLYCEROL WHICH IS CONVERTED TO METHANOL

(75) Inventors: Duane Goetsch, Andover, MN (US); Ian S. Machay, Eden Prairie, MN (US); Lloyd R. White, Minneapolis, MN (US)

(73) Assignee: G.D.O. Inc., Elk River, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 11/824,919

(22) Filed: Jul. 3, 2007

(51) Int. Cl.
*C07C 27/06* (2006.01)
(52) U.S. Cl. .................. 518/703; 518/702; 518/704
(58) Field of Classification Search ......... 518/702–704
See application file for complete search history.

(56) References Cited

U.S. PATENT DOCUMENTS 5,344,848 A * 9/1994 Steinberg et al. ............ 518/704

OTHER PUBLICATIONS

Borgwardt, R.H. (1998). Ind. Eng. Chem. Res., 37(9), 3760-3767.*
Dong, Y. et al (1998). Energy Fuels, 12(3), 479-484.*
Dong, Y. et al. (1997). Int. J. Hydrogen Energy, 22(10/11), 971-977.*
Demirbas, A. (2005). Progress in Energy and Combustion Science, 31, 466-487.*

* cited by examiner

*Primary Examiner*—Robert J Hill, Jr.
*Assistant Examiner*—Brian McCaig
(74) *Attorney, Agent, or Firm*—Henry E. Naylor

(57) ABSTRACT

Production of biodiesel from vegetable and animal oils with conversion of a by-product crude glycerol stream to methanol. The crude glycerol stream is combined with superheated steam and oxygen to produce a synthesis gas that is then passed to a methanol synthesis reaction zone to produce methanol.

21 Claims, 1 Drawing Sheet

PRODUCTION OF BIODIESEL AND A SIDE STREAM OF CRUDE GLYCEROL WHICH IS CONVERTED TO METHANOL

FIELD OF THE INVENTION

The present invention relates to the production of biodiesel from vegetable and animal oils with conversion of a by-product crude glycerol stream to methanol. The crude glycerol stream is combined with superheated steam and oxygen to produce a synthesis gas that is then passed to a methanol synthesis reaction zone to produce methanol.

BACKGROUND OF THE INVENTION

There has been an increasing interest in biodiesel fuels as a supplement to, or replacement for, traditional fossil fuels. The term "biodiesel" is used for a variety of ester-based oxygenated fuels made from vegetable oils, fats, greases, or other sources of triglycerides. It is a nontoxic and biodegradable substitute and supplement for petroleum diesel. Even in blends as low as 20% biodiesel and 80% petroleum diesel (B20), biodiesel can substantially reduce the emission levels and toxicity of diesel exhaust. Biodiesel has been designated as an alternative fuel by the United States Department of Energy and the United States Department of Transportation, and is registered with the United States Environmental Protection Agency as a fuel and fuel additive. It can be used in any diesel engine, without the need for mechanical alterations, and is compatible with existing petroleum distribution infrastructure.

Biodiesel processing involves the production of alkyl esters of long chain fatty acids by reacting the source acid with a low molecular weight alcohol, such as methanol or ethanol. A traditional process for manufacturing fatty acid alkyl esters involves the transesterification of triglycerides using methanol, in the presence of an alkali catalyst. In addition to the desired fatty acid alkyl esters, this process produces an effluent stream comprising glycerol (glycerol), excess alcohol, water, alkyl esters and a mixture of mono, di and triglycerides resulting from the transesterification step. The rapid worldwide expansion of the production of biodiesel fuel since 2000 is creating a rapidly growing supply of byproduct crude glycerol. Over the past year or so the value of crude glycerol has decreased and it is anticipated that biodiesel producers may receive little or no value for this material. A biodiesel plant producing approximately 30,000,000 gallons per year of product generates approximately 22 million pounds of crude glycerol and requires approximately 26 million pounds of methanol (460,000 gallons).

At one time there was a valuable market for glycerol, which assisted the economics of the biodiesel process as a whole. However, with the increase in global biodiesel production, the market price for crude glycerol has crashed. Thus, there is a need in the art for processes capable of converting crude glycerol to more valuable products as well as for reducing the amount of methanol purchased by biodiesel producers from third party sources.

SUMMARY OF THE INVENTION

In accordance with the present invention, there is provided a process for producing biodiesel and a crude glycerol by-product which is converted to methanol, which method comprises:

i) providing a mixture of at least one $C_1$ to $C_4$ alcohol and a transesterification catalyst;

ii) conducting said mixture, along with a triglyceride feedstream, to a transesterification reaction zone operated at tranesterification conditions thereby resulting in a transesterification reaction product stream comprised of alkyl esters, crude glycerol, unreacted alcohol, and transesterification catalyst;

iii) treating said product stream with a neutralizing agent thus neutralizing the reaction product stream;

iv) conducting said neutralized product stream to a first separation zone wherein at least a fraction of the crude glycerol is separated from said product stream, thus resulting in a crude glycerol stream and a crude glycerol lean product stream;

v) separating the unreacted alcohol from the crude glycerol product stream;

vi) collecting the alkyl ester biodiesel product;

vii) introducing crude glycerol, an effective amount of superheated steam, and an effective amount of oxygen into a reaction zone where the resulting mixture is heated to a temperature of about 1500° F. to about 1900° F. and at pressures from about 200 psig to about 600 psig, thereby resulting in a synthesis gas product stream comprised predominantly of $H_2$ and CO with minor amounts of $CO_2$ and having a temperature substantially that of the reaction zone;

viii) cooling said synthesis gas product stream to a temperature of about 360° F. to about 80° F.;

ix) pressurizing the cooled synthesis gas product stream to a pressure of about 500 psig to about 1500 psig;

x) introducing said pressurized cooled synthesis gas into a methanol synthesis reaction zone along with an effective amount of methanol synthesis catalyst, which methanol synthesis reaction zone is maintained at a temperature from about 350° F. to about 450° F. and pressures from about 500 psig to about 1500 psig, thereby resulting in a product stream comprised of methanol and water;

xi) conducting the methanol synthesis product stream to a second separation zone wherein a tail gas stream is separated from a liquid product stream, which liquid product stream is comprised of methanol and water;

xii) conducting said mixture of methanol and water to a third separation zone wherein substantially all of the methanol is separated from the water;

xiii) conducting said liquid product from said separation zone to a distillation zone wherein methanol is separated from said water component;

xiv) separately collecting the methanol and water.

In a preferred embodiment, the gasification reaction zone is an autothermal reaction zone.

In another preferred embodiment, the product gas stream exiting the reaction zone is cooled in multiple steps.

In another preferred embodiment, the gas exiting the separation zone is further separated via the use of membranes to 1) produce a hydrogen enriched gas to recycle to the methanol synthesis reactor and or 2) reject carbon dioxide.

In another preferred embodiment, an effective amount of steam is added to the compressed stream being conducted to the methanol reaction zone.

In yet another preferred embodiment, an effective amount of hydrogen is added to the compressed stream being conducted to the methanol reaction zone.

BRIEF DESCRIPTION OF THE FIGURE

The FIGURE hereof is a simplified flow diagram of a preferred embodiment of the present invention showing process steps for producing biodiesel from a triglyceride source with a crude glycerol side stream which is converted to methanol.

DETAILED DESCRIPTION OF THE INVENTION

Figure 1:
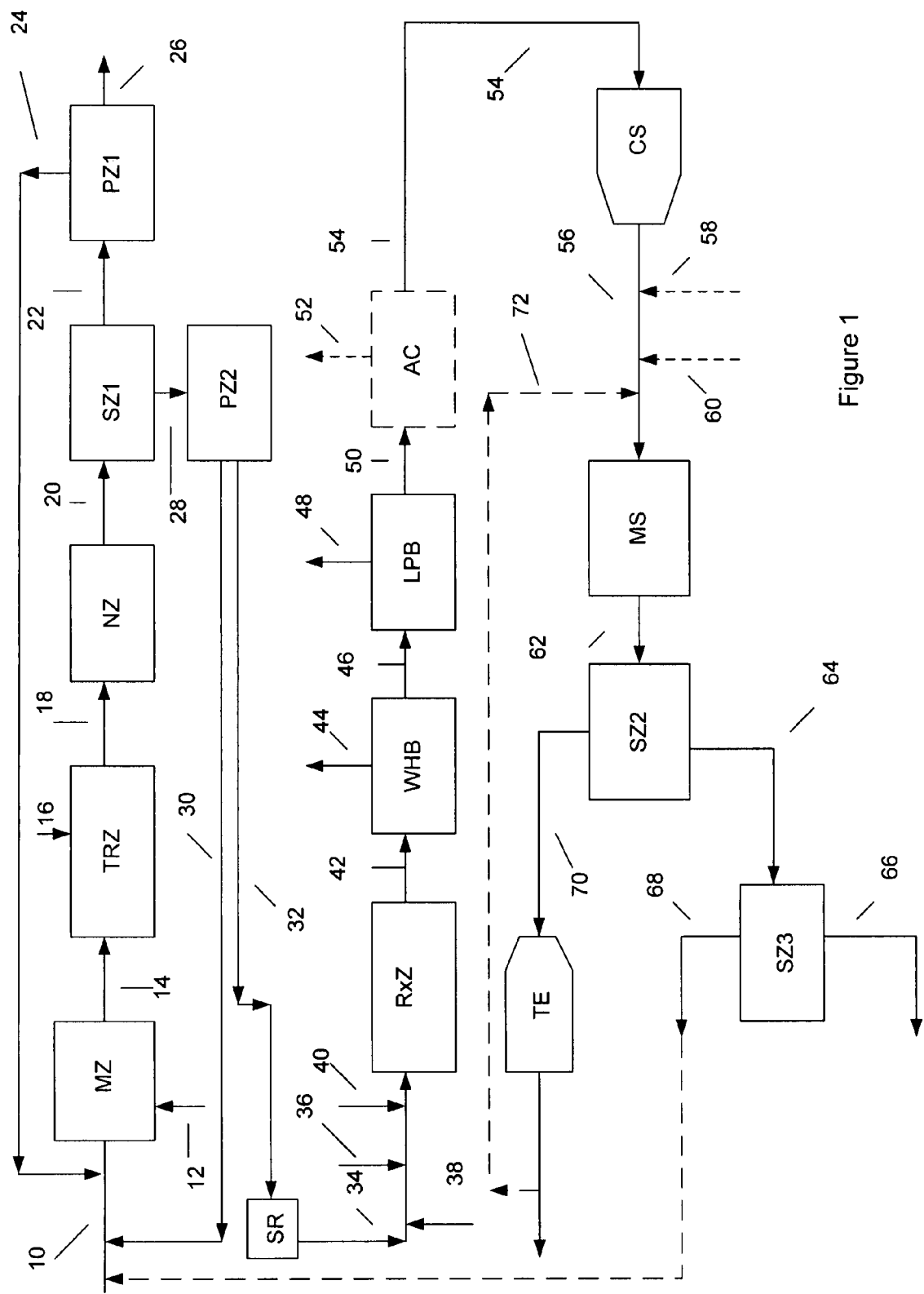

The present invention relates to a process for the production of biodiesel with conversion of the by-product crude glycerol to methanol. The crude glycerol by-product stream from a biodiesel plant id typically comprised of a mixture of glycerol, methanol, water, inorganic salts (catalyst residue) free fatty acids, unreacted mono-, di-, and triglycerides, methyl esters, as well as a variety of other matter organic non-glycerol (MONG) in varying quantities. The methanol is typically stripped from this stream and reused, leaving behind, after neutralization, what is known as crude glycerol. In raw form, this crude glycerol has a high salt and free fatty acid content and substantial color (yellow to dark brown). Consequently, crude glycerol has few direct uses due to the presence of the salts and other species, and its fuel value is marginal. The US biodiesel industry generates millions of gallons of crude glycerol by-product each year, and the amount produced is growing rapidly along with the dramatic growth of biodiesel production.

Thus, the combination of high methanol prices, low glycerol prices and the availability of sufficient by-product crude glycerol, have made the present invention commercially attractive for the establishment of small economical methanol production facilities that can be integrated with existing biodiesel plants. The process of the present invention can be scaled to any size biodiesel facility, but it is preferred that the facility be relatively large, for example in excess of 20 million gallons per year of biodiesel production. Power generation can also be added to the process to off-set future costs in electricity.

The process of the present invention can better be understood with reference to the figures hereof, which is a simplified process scheme for the production of biodiesel from a triglyceride source resulting in a crude glycerol side stream that is converted to methanol. An effective amount of alcohol is conducted via line 10 to a mixing zone MZ. The effective amount of alcohol, for this reaction will be about 10 wt. % alcohol, based on the weight of triglyceride (vegetable or animal oil) feed. That is, for every 100 lbs of vegetable or animal oil feed 10 lbs of alcohol will be used. The alcohol can be any $C_1$ to $C_4$ alcohol, but it is preferred that it be selected from methanol and ethanol, with methanol being preferred. An effective amount of suitable catalyst is conducted via line 12 to the mixing zone MZ. By "effective amount" of catalyst we mean that minimum amount needed to catalyze the transesterification reaction but not so much as to cause undesirable results or that will add too much of a cost burden to the process. The catalyst used can be a basic catalyst, an acid catalyst, or an enzyme catalyst. Non-limiting examples of basic catalysts that can be used in the practice of the present invention includes sodium hydroxide, potassium hydroxide, diethylamine (DEA), dimethylethanol amine (DMAE), tetramethyldiaminoethane (TEMED), and tertramethylammonium hydroxide (TMAH). Non-limiting examples of acid catalysts that can be used in the practice of the present invention includes sulfuric acid, hydrochloric acid, calcium acetate, barium acetate, carboxylic salts of metals (Cd, Mn, Pb, and Zn), and solid acid catalysts. A non-limiting example of a preferred enzyme catalyst is lipase. Basic catalysts are preferred.

The alcohol and catalysts are mixed in mixing zone MZ. After effective mixing, the mixture is conducted via line 14 to transesterification reaction zone TRZ. A suitable triglyceride feedstock is introduced into transesterification zone TRZ via line 16. Non-limiting examples of preferred sources of triglycerides include vegetable oils, animal oils, and animal fats. In transesterification reaction zone TRZ, the alcohol/catalyst mixture is reacted with the triglycerides in a closed reaction vessel at a temperature of about the boiling point of the alcohol. For methanol, the temperature will be from about 70° F. to about 150° F. The pressure of the transesterifaction zone TRZ will preferably be about atmospheric pressure, although higher pressures can also be used. The transesterification reaction will proceed for an effective amount of time. By "effective amount of time" we mean at that amount of time needed for at least about 90 wt. %, preferably at least about 95 wt. %, more preferably at least about 98 wt. % and most preferably substantially all of the triglycerides to be converted to the corresponding alkyl esters. This effective amount of time will typically be from about 1 hour to about 24 hours. The resulting product stream is a mixture of glycerol, biodiesel, alcohol and catalyst which is conducted via line 18 to neutralization zone NZ. In neutralization zone NZ, the mixture is neutralized by any suitable conventional neutralization technology. The particular neutralization technology used will depend on the type of catalyst used in the transesterification reaction.

The resulting neutralized mixture is conducted via line 20 to a first separation zone SZ1, wherein the crude biodiesel product containing unreacted alcohol is separated from the crude glycerol by-product which also may contain some unreacted alcohol. Non-limiting examples of examples of suitable separation techniques that can be used for this first separation zone include gravity separation and centrifugation. The crude biodiesel is conducted via line 22 to first purification zone PZ1. In first purification zone PZ1, the alcohol is separated from the crude biodiesel and either collected or recycled via line 24. This removes residual catalyst and soaps from the crude biodiesel. The alcohol, which is separated from the crude biodiesel is recycled via line 24 to mixing zone MZ. It will be understood that the alcohol can also be introduced directly (not shown) into the transesterification reaction zone TRZ. A purified biodiesel product is recovered via line 26 The crude glycerol from first separation zone SZ1 is conducted via line 28 to second purification zone PZ2. In purification zone PZ2, unreacted alcohol, if present, is separated from the crude glycerol using any suitable means such as flash evaporation or distillation. The additional unreacted alcohol is recycled via line 30 to mixing zone MZ or in the alternative to the transesterification zone or both. The crude glycerol is conducted via line 32 to a process train wherein it is converted to methanol. The crude glycerol is conducted via line 32 to salt removal zone SR remove any remaining salts. The salts to be removed will depend on the catalyst used for the production of the biodiesel. For example, if the transesterification zone of the biodiesel process was base catalyzed and if the base was $CH_3ONa$ and neutralized with HCL, then the salt will be NaCl. If the base was $CH_3OK$, then the salt will be KCl. The salt removal zone SR can be comprised of any suitable technology capable of removing salts. Non-limiting examples of technologies that can be used in the practice of the present invention for the salt removal zone include vacuum distillation, reverse osmosis, electropherisis, electrodialysis, or a combination thereof. Preferred is electrodialysis. The resulting substantially salt-free glycerol is passed via line 34 to a reaction zone GZ, which is preferably a gasification zone, more preferably an autothermal reaction zone wherein the crude glycerol is gasified to a synthesis gas. An effective amount of oxygen is also conducted to into reaction zone RxZ via line 36. The oxygen can be obtained from any suitable source, but a preferred source is to produce it on site. This can be done by passing air though a pressure swing adsorption unit (not shown) containing an adsorbent that is more selective for nitrogen then oxygen, thus resulting in an oxygen-rich stream and a nitrogen-rich stream. The oxygen-rich stream is passed to reaction zone RxZ via lines 36 and 34 and a nitrogen-rich stream is vented (not shown) into the atmosphere.

An effective amount of steam is introduced via line 38. It is preferred that the steam be superheated steam. The superheated steam, which will be at a temperature from about 315° C. to about 700° C., acts as both a source of hydrogen as well as to prevent coking. The amount of superheated steam to feedstock will be an effective amount. By effective amount we mean at least that amount needed to prevent coking in reaction zone RXZ. The ratio of superheated steam to crude glycerol, on a volume to volume basis, will typically be from about 0.2 to 2.5, preferably from about 1.5 to 2.5 and more preferably about 2.2. The mixture of steam and crude glycerol feed will preferably be at a temperature above its dew point, which will typically be greater than about 230° C. It is preferred that an effective amount of an additional organic material (co-feed) be introduced via lines 40 and 34. Non-limiting examples of suitable additional organic materials include free fatty acids, animal fats, oils and organic compounds derived from biomass processing. Preferred are free fatty acids. By effective amount of organic material we mean that amount that will substantially increase the yield of methanol. By substantially increase the yield of methanol we mean at least that amount needed that will result in an increase in the methanol yield by at least about 5 vol. %, more preferably by at least about 10 vol. % over the case where no additional organic material is added. Such an amount can be calculated from the preferred ratio of $H_2$ to CO without producing an undesirable amount of $CO_2$. Non-limiting examples of free fatty acids suitable for use herein include the $C_{14}$ to $C_{20}$ carboxylic acids.

The feed mixture is reacted in reaction zone RxZ at temperatures from about 1500° F. to about 1900° F., preferably from about 1600° C. to about 1800° C. The pressure in reaction zone RxZ will be from about 200 psig to about 600 psig, preferably from about 360 psig to about 440 psig. An autothermal reaction is preferred over other type of reaction zones because in autothermal mode the heating is done directly from products produced during the reaction. That is, once the reaction is initiated with an effective amount of heat, the reaction is self supporting from fuel products resulting from the reaction. Direct heating helps to prevent coking that would more likely result from indirect heating. Within the autothermal reaction zone a combination of partial oxidation, hydrogen reforming, methanation, and a water shift reaction will occur. The autothermal reaction zone is preferably operated adiabatically and the composition of the resulting product gas will be based on the approach to equilibrium. For example, the mole ratios of steam to reduced carbon and oxygen to reduced carbon as well as the amount of oxygen used in the feed will determine the precise composition of the product gas. It is within the scope of this invention that a suitable catalyst be used in reaction zone RxZ which catalyst will typically be a nickel based catalyst. The feed composition to reaction zone RxZ can vary depending on the amount of methanol one wishes to produce in a single pass process system and on the amount of carbon in the organic material co-feed, if used. It is desirable to keep the steam/reduced carbon ratios sufficiently high enough to avoid carbon formation. However the need to produce CO (leads to higher methanol production) limits the maximum value of this ratio. For example, as the concentration of steam is increased, the less likely it will be that coke will form but an increase of $CO_2$ will result with a corresponding decrease in methanol yield. The resulting syngas product will most typically be comprised of about 10-15 vol. % $CO_2$ with the remainder being about a 1:1 ratio of $H_2$:CO.

The product synthesis gas, which is comprised primarily of $H_2$ and CO with minor amounts of $CO_2$, from reaction zone RxZ is cooled to an effective temperature wherein it can be fed to methanol synthesis zone MS. The FIGURE hereof shows multi-step cooling that is preferred to capture as much of the heat energy as possible. For example, the synthesis gas product stream from the reaction zone is conducted, via line 42 to waste heat boiler WHB wherein high pressure steam 44 is generated which can be utilized for heating requirements at the biodiesel site. It can also be used for supplying heat to other processes, such as the crude glycerol cleanup or methanol recovery. The production of high pressure steam requires an exit temperature from the waste heat boiler WHB of about 600° F. or higher. The exit gas from waste heat boiler WHB is passed via line 46 to low pressure boiler LPB which further cools the gas from ≧600° F. to a pressure suitable for low pressure steam (typically between 30 and 150 psig shown by line 48). In one embodiment of the present invention, the cool-down of the product stream can be passed via line 50 to an additional cooling step AC to make extremely low pressure steam, or hot water, while making an intermediate pressure steam in the range of 150 psig (350° F.). This final cooling step AC involves lowering the exit gas temperature to near ambient temperature or at least below about 140° F., in order to reduce the water content prior to subsequent compression. The heat rejected from this final cooling step can be utilized as hot water 52. Some synthesis gas cleanup may be necessary in order to remove any residual solids or unwanted compounds such as sulfur, ammonia, or both. The recovered water can be recycled (not shown) to reaction zone RxZ. Residual solids and unwanted dissolved gases, such as $NH_3$, or possibly other acid gases can be stripped prior to re-use of the water.

The resulting cooled synthesis gas is than conducted via line 54 to compression stage CS. In one embodiment, a $CO_2$ scrubbing stage (not shown) can be utilized to increase the partial pressure of $H_2$ and CO by the removal of at least a portion of any $CO_2$. The pressure of the product gas stream is increased in compression stage CS to at least about 1500 psig, which is necessary in order to achieve a better methanol yield. The resulting compressed synthesis gas stream 56 can be optionally be combined with water, preferably in the form of steam, via line 58 in order to increase the $H_2$ content (through usage of CO) via the shift reaction. The shift step (not shown) can be used in a separate step or part of the overall methanol reactor system. It is optional that hydrogen via line 60 be added to the compressed feed being conducted to methanol synthesis reactor MS. Methanol synthesis is well known in the art and it is generally performed by passing a synthesis gas comprising hydrogen, carbon oxides and any inert gasses at an elevated temperature and pressure through one or more beds of a methanol synthesis catalyst, which is typically a copper-containing catalyst composition. Methanol is generally recovered by cooling the product gas stream to below the dew point of the methanol and separating the product as a liquid. Preferably, the methanol synthesis reactors are fixed bed reactors with provisions for heat transfer within the catalyst bed(s). Particularly preferred reactors are fixed bed reactors with heat transfer tubes or coils within the catalyst beds. The catalyst may be either inside or outside of the heat transfer tubes, with the cooling fluid on the other side. Multiple cooling tubes can be inside a single reactor. The catalyst bed may also be a fluid bed that is fluidized with a suitable fluid, either gas, liquid, or both. In one embodiment, at least one reactor is a fixed bed reactor having multiple cooling tubes (e.g., coils) spaced within a catalyst bed. In another embodiment, at least one reactor contains multiple tubes, each packed with catalyst, and surrounded by a heat transfer medium.

The catalyst used in the methanol synthesis process is preferably a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc. The methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst. More preferred catalysts for methanol synthesis are those available from Johnson Matthey under the KATALCO 51 Series tradename as well as those available from Haldo-Topsoe under the MK-121 tradename.

The methanol synthesis is performed at pressures in the range of about 40 to about 150 bar absolute, preferably in the range of about 50 to about 120, bar absolute, and more preferably in the range of about 50 to 100 bar absolute. The temperature of the synthesis catalyst is suitably in the range of about 300° to about 570° F., preferably from about 325° to about 500° F., and more preferably from about 350° to about 475° F. The synthesis gas preferably enters the catalyst beds at a temperature in the range of about 200° to about 250° C. and leaves the catalyst beds at temperatures preferably in the range of about 2200 to about 260° C. Such temperatures provide for an acceptable methanol output rate (owing to favorable equilibrium) without producing the greater content of by-product impurities, and reduction in catalyst life, that would result from operation at higher temperatures. In a single pass configuration, the catalyst volume is selected to allow near equilibrium conversion. This value is typically in the range of 1500 GHSV with an ideal feed ($H_2/CO=2.1$) with small amounts of $CO_2$ (<10%). Higher concentrations of $CO_2$ and/or lower $H_2/CO$ ratios will require larger catalyst volumes.

Returning now to the FIGURE, it is preferred to add hydrogen via line 60 to enhance methanol yields. The product stream from methanol synthesis zone MS is passed via line 62 to a second separation zone SZ2, which is preferably a flash drum wherein methanol and water and heavier products are condensed out from unreacted gases (tail gas). The water/methanol mixture is passed from second separation zone SZ2 via line 64 to third separation zone SZ3, which is preferably a distillation zone wherein water and heavy products, such as dimethylethers are separated and collected via line 66. The water can be re-used to produce steam and recycled. The methanol is collected via line 68 and can be stored, transported, sold or recycled to mixing zone MZ and/or directly to transesterification zone TRZ. A tail gas (unreacted syngas with a lower heating value) stream is collected from third separation zone SZ3 via line 70, which is preferably sent through turboexpander TE that recovers the energy from gas expansion and cools the tail gas. When a turboexpander is used the energy can either be recovered with a shaft coupled electric generator or with a shaft coupled compressor. This minimizes overall energy consumption. The tail gas will typically be comprised of hydrogen and carbon monoxide and can be used for local steam and heating requirement. The tail gas can also be recycled, via line 72, to the methanol synthesis reaction zone, but it is preferred to operate the methanol synthesis reaction zone on a once through basis and the unreacted tail gas used for fuel replacement.

What is claimed is:

1. A process for producing biodiesel and a crude glycerol by-product which is converted to methanol, which method comprises:
   i) providing a mixture of at least one $C_1$ to $C_4$ alcohol and a transesterification catalyst;
   ii) conducting said mixture, along with a triglyceride feedstream, to a transesterification reaction zone operated at transesterification conditions thereby resulting in a transesterification reaction product stream comprised of alkyl esters, crude glycerol, unreacted alcohol, and transesterification catalyst;
   iii) treating said product stream with a neutralizing agent thus neutralizing the reaction product stream;
   iv) conducting said neutralized product stream to a first separation zone wherein at least a fraction of the crude glycerol is separated from said product stream, thus resulting in a crude glycerol stream and a crude glycerol lean product stream;
   v) separating the unreacted alcohol from the crude glycerol product stream;
   vi) collecting the alkyl ester biodiesel product;
   vii) introducing crude glycerol, an effective amount of superheated steam, and an effective amount of oxygen into a reaction zone where the resulting mixture is heated to a temperature of about 1500° F. to about 1900° F. and at pressures from about 200 psig to about 600 psig, thereby resulting in a synthesis gas product stream comprised predominantly of $H_2$ and CO with minor amounts of $CO_2$ and having a temperature substantially that of the reaction zone;
   viii) cooling said synthesis gas product stream to a temperature of about 360° F. to about 80° F.;
   ix) pressurizing the cooled synthesis gas product stream to a pressure of about 500 psig to about 1500 psig;
   x) introducing said pressurized cooled synthesis gas into a methanol synthesis reaction zone along with at effective amount of methanol synthesis catalyst, which methanol synthesis reaction zone is maintained at a temperature from about 350° F. to about 450° F. and pressures from about 500 psig to about 1500 psig, thereby resulting in a product stream comprised of methanol, water and heavier products;
   xi) conducting the methanol synthesis product stream to a second separation zone wherein a tail gas stream is separated from a liquid product stream, which liquid product stream is comprised of methanol and water;
   xii) conducting said mixture of methanol and water to a third separation zone wherein substantially all of the methanol is separated from the water;
   xiii) conducting said liquid product from said separation zone to a distillation zone wherein methanol is separated from said water component;
   xiv) separately collecting the methanol and water.

2. The process of claim 1 wherein the $C_1$ to $C_2$ alcohol is selected from methanol and ethanol.

3. The process of claim 2 wherein the alcohol is methanol.

4. The process of claim 3 wherein at least a fraction of the unreacted alcohol of step v) is recycled to the mixing zone, the transesterification zone, or both.

5. The process of claim 3 wherein the catalyst of the methanol synthesis reaction zone is a copper based catalyst.

6. The process of claim 5 wherein the temperature of the methanol synthesis reaction zone is from about 325° F. to about 500° F. and the pressure is from about 50 to about 100 bar absolute.

7. The process of claim 6 wherein the gasification reaction zone is an autothermal reaction zone.

8. The process of claim 7 wherein the first separation zone is a flash drum.

9. The process of claim 7 wherein the second separation zone is a distillation zone.

10. The process of claim 9 wherein an organic material co-feed is introduced in to the reaction zone with the crude glycerin.

11. The process of claim 10 wherein the organic material is selected from the group consisting of free fatty acids, animal fats, oils and organic compounds derived from biomass processing.

12. The process of claim 10 wherein an effective amount of steam is added to the pressurized cooled synthesis gas.

13. The process of claim 12 wherein an effective amount of water is added to the pressurized cooled synthesis gas.

14. The process of claim 1 wherein the reaction zone is an autothermal reaction zone.

15. The process of claim 1 wherein the first separation zone is flash drum.

16. The process of claim 1 wherein the second separation zone is a distillation zone.

17. The process of claim 1 wherein an organic material co-feed is introduced in to the reaction zone with the crude glycerin.

18. The process of claim 17 wherein the organic material is selected from the group consisting of free fatty acids, animal fats, oils and organic compounds derived from biomass processing.

19. The process of claim 1 wherein an effective amount of steam is added to the pressurized cooled synthesis gas.

20. The process of claim 1 wherein an effective amount of hydrogen is added to the pressurized cooled synthesis gas.

21. The process of claim 1 wherein the tail gas product is recycled to the pressurized cooled synthesis gas.

* * * * *